US005443828A

United States Patent [19]

Kang et al.

[11] Patent Number: 5,443,828

[45] Date of Patent: Aug. 22, 1995

[54] CHIMERIC HIV-2 GAG PARTICLES

[75] Inventors: Chil-Yong Kang; Lizhong Luo, both of London, Canada

[73] Assignee: Korea Green Cross Corporation, Rep. of Korea; a part interest

[21] Appl. No.: 992,618

[22] Filed: Dec. 18, 1992

[30] Foreign Application Priority Data

Jun. 17, 1992 [KR] Rep. of Korea .............. 10493/1992

[51] Int. Cl.⁶ ...................... A61K 39/21; C12N 15/48; C12N 15/49

[52] U.S. Cl. ............................... 424/188.1; 435/69.3; 435/172.3; 424/207.1; 424/208.1; 424/184.1; 424/185.1; 424/186.1; 424/187.1; 530/350; 530/826; 536/23.1; 536/23.4; 536/23.7; 536/23.72

[58] Field of Search ............ 424/88, 89, 185.1, 186.1, 424/187.1, 188.1, 207.1, 208.1, 184.1; 435/69.3, 69.7, 172.3; 530/350, 826; 536/23.4, 23.1, 23.7, 23.72; 935/47

[56] References Cited

U.S. PATENT DOCUMENTS 4,925,784 5/1990 Crowl et al. .......................... 435/5

OTHER PUBLICATIONS

Wagner, R. et al. Abstract from: Int. Conf. AIDS Jun. 20–23, 1990.

Guyader, M. et al. Nature 326: 662–669 (1987).

Norley, S. et al. Immunobiology 184: 193–207 (1992).

Adams, S. et al Abstract from: AIDS: Antiviral therapy/Immunotherapy/Gene therapy/Sep. 1–8, 1991.

Wagner, R et al. Abstract from: Int. Conf. AIDS Jun. 16–21, 1991.

Griffiths, J. et al. Abstract from: Int Conf. AIDS Jun. 16–21, 1991.

W. G. Robey et al., "Prospect for Prevention of Human Immunodeficiency Virus Infection: Purified 120–kDa Envelope Glycoprotein Induces Neutralizing Antibody", *Proc. Natl. Acad. Sci. USA,* 83:7023–7027, Sep. 1986.

Per A. Broliden et al., "A Monoclonal Antibody to Human Immunodeficiency Virus Type 1 Which Mediates Cellular Cytotoxocity and Neutralization", *Journal of Virology,* 64:No. 2:936–940, Feb. 1990.

Hidemi Takahashi et al., "An Immunodominant Epitope of the Human Immunodeficiency Virus Envelope Glycoprotein gp160 Recognized by Class I Major Hisitocompatibility Complex Molecule–restricted Murine Cytotoxic T Lymphocytes", Proc. Natl. Acad. Sci. USA, 85:3105–3109, May 1988.

Hidemi Takahashi et al., "Induction of Broadly Cross––Reactive Cytotoxic T Cells Recognizing an HIV–1 Envelope Determinant", *Science,* 255:333–336, 17 Jan. 1992.

Gregory J. LaRosa et al., "Conserved Sequence and Structural Elements in the HIV–1 Principal Neutralizing Determinant", *Science,* 249:932–935, 24 Aug. 1990.

Mark L. Huang et al., "Localization of Immunogenic Domains in the Human Immunodeficiency Virus Type 2 Envelope", *Journal of Virology,* 65:No. 9:5073–5079, Sep. 1991.

Ewa Bjorling et al., "Hyperimmune Antisera Against Synthetic Peptides Representing the Blycoprotein of Human Immunodeficiency Virus Type 2 Can Mediate Neutralization and Antibody–Dependent Cytotoxic Activity", *Proc. Natl. Acad.* Sci. USA, 88:6082–6086, Jul. 1991.

(List continued on next page.)

*Primary Examiner*—Christine M. Nucker
*Assistant Examiner*—M. Tuscan
*Attorney, Agent, or Firm*—Merchant, Gould, Smith, Edell, Welter & Schmidt

[57] ABSTRACT

The chimeric proteins, and a protential vaccine and diagnostic reagent comprising gag-env chimeric protein particles are disclosed. The preparation comprises linking gag of HIV-2 to env to form the chimeric gene, inserting the obtained chimeric gene into the DNA of a baculovirus, infecting insect cells or insect host with the resulting recombinant virus, culturing it and purifying the obtained chimeric protein. The gag chimeric protein of HIV according to the present invention retains both antigenic and immunogenic properties.

4 Claims, 11 Drawing Sheets

OTHER PUBLICATIONS

Lizhong Luo et al., "Expression of gag Precursor Protein and Secretion of Virus-like gag Particles of HIV-2 from Recombinant Baculovirus-Infected Insect Cells", Virology, 179:874-880, 1990.

C. Yong Kang, "Baculovirus Vectors for Expression of Foreign Genes", Advances in Virus Research, 35:177-192, 1988.

U. K. Laemmmli, "Cleavage of Structural Proteins during the Assembly of the Head of Bacteriophage T4", *Nature,* 227:680-685, 15 Aug. 1970.

Kenneth Garson et al., "The N-Terminal env-Derived Amino Acids of v-re1 are Required for Full Transforming Activity", *Virology,* 177:106-115, 1990.

Wing L. Sung et al., "Synthesis of Mutant Parathyroid Hormone Genes Via Site-Specific Recombination Directed by Crossover Linkers", *Gene,* 47:261-267, 1986.

Phillip W. Berman et al., "Protection of Chimpanzees from Infection by HIV-1 after Vaccination with Recombinant Glycoprotein gp120 but not gp160", *Nature,* 345:622-625, 14 Jun. 1990.

Marc Girard et al., "Immunization of Chimpanzees Confers Protection Against Challenge with Human Immunodeficiency Virus", *Proc. Natl. Acad. Sci. USA,* 88:542-546, Jan. 1991.

Scott D. Putney et al. "HTLV-III/LAV-Neutralizing Antibodies to an *E. coli*-Produced Fragment of the Virus Envelope", *Science,* 234:1392-1395, 12 Dec. 1986.

| MUTANT | SITE-SPECIFIC MUTAGENESIS | PARTICLE FORMATION |
|---|---|---|
| HIV2-gag$_{380}$-W | N —— 373 CCA Pro / 375 CCC Pro / 377 CCA Pro —— C | + |
| HIV2-gag$_{380}$-1 | N —— CCA / CCC Pro / CTA Leu —— C | + |
| HIV2-gag$_{380}$-2 | N —— CCA / CTC Leu / CTA Leu —— C | + |
| HIV2-gag$_{380}$-3 | N —— CTC Leu / CTC Leu / CTA Leu —— C | −

HIV-1 gp120 GENE IN pUC19

HIV-2 gp120 GENE IN pUC18

Creation of BglII site by crossover linker mutagenesis

Insertion of gp120 BglII fragment into BglII site of gag gene

M 1 2 Wt C

M 1 2 Wt C

88—
47—
33—

CHIMERIC HIV-2 GAG PARTICLES

BACKGROUND OF THE INVENTION

1. Field of the Invention

The present invention relates to construction of chimeric proteins useful in a potential AIDS vaccine, for development of diagnostic reagents and a process for production thereof. More particularly, the present invention relates to gag chimeric proteins of HIV expressed in recombinant baculovirus infected insect cells, and a process for production thereof. 2. Description of the Prior Art Types 1 and 2 of the human immunodeficiency viruses (HIV) are recognized as the etiologic agents for acquired immunodeficiency syndrome (AIDS). A vaccine against those viruses would be an ideal way to prevent the development of AIDS from infection with HIV. There has been much research focused on molecular biological analyses of structures and functions of HIV. The main virion structural proteins of HIV are derived from the three structural genes known as gag, pol, env. The genome of many different isolates of HIVs have been completely sequenced and amino acids sequences have been deduced from the cloned proviral DNA sequences. The envelope gene of HIV codes for a glycoprotein precursor with a molecular weight 160,000 (gp160). The precursor gp160 in virus infected cells is processed (or cleaved) to produce envelope glycoprotein gp120 and gp41. The envelope glycoprotein gp120 of HIV has been the major target for developing a candidate vaccine against AIDS. gp120 recognizes the cellular receptor (CD4) on helper T lymphocytes and carries the V3 loop domain that induces neutralizing antibodies (Science 234, 1392–1395, 1986; Proc. Natl. Acad. Science, USA 83, 7023–7027).

The V3 loop represents the third hypervariable region of HIV-1 gp120 (amino acid residues 308–331) which contains not only a major immunodominant neutralizing epitope but also the epitopes for antigen-dependent cellular cytotoxicity (ADCC) and cytotoxic T-lymphocyte (CTL) recognition. Although the majority of the amino acids in the V3 loop are variable among different strains of HIV, a G-P-G-R motif at the tip of the loop is conserved (Science 249, 932–935, 1990).

Recently, Huang et al. and Björling et al. demonstrated that the principal neutralization domain of the envelope glycoprotein of HIV-2 is also located in the region corresponding to the hypervariable motif in the V3 loop of HIV-1 gp120. The CD4-binding region, which is located within the C-terminal third of HIV-1 gp120 (amino acid residues 397–439) plays an essential role in infectivity of HIV. This region also seems to be weakly immunogenic because it forms a pocket which is not accessible to the immune system. Thus high-titre neutralizing antibody against this region is not presently available.

SUMMARY OF THE INVENTION gag-env chimeric proteins can be obtained by linking gag of HIV to env to form a chimeric gene, inserting the chimeric gene into the DNA of a baculovirus, infecting the resulted recombinant virus with the insect cells or insect, culturing it and purifying the obtained chimeric protein. Such chimeric proteins may be used for preparing a potential AIDS vaccine.

BRIEF DESCRIPTION OF THE DRAWINGS

The invention will be described in detail with reference to the accompanying drawings in which.

Other objects, features and advantages of the invention will hereinafter become more readily apparent from the following description.

DETAILED DESCRIPTION OF THE PREFERRED EMBODIMENTS

The present invention provides the gag chimeric protein of HIV, which retains both antigenic and immunogenic properties of gag, and a portion of an env protein.

The present inventors reported previously that expression of the gag coding sequences of HIV-2, lacking the protease gene, in insect cells produced virus-like particles (Virology 179, 874–880, 1990).

Figure 1:
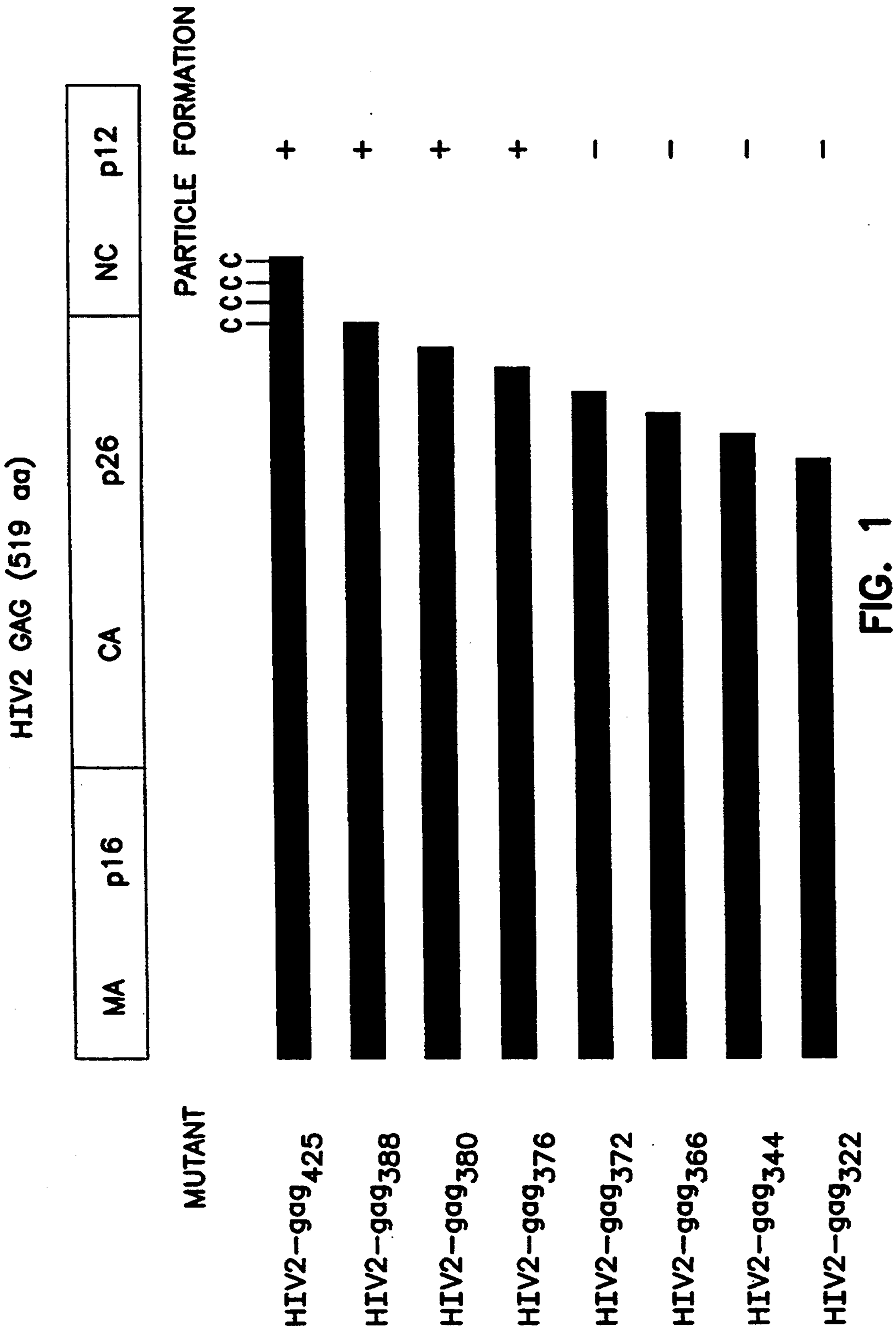
FIG. 1 shows deletion mutants of HIV-2 gag gene and particle formation. A series of deletion mutants of HIV-2 gag gene were constructed by PCR with specific primers and the size of the deletion mutant are indicated by the amino acid numbers which are retained. Deletion routants of HIV-2-$gag_{425}$, -$gag_{388}$, -$gag_{380}$, and -$gag_{376}$ formed virus-like particles and were released into culture medium, whereas deletion mutants HIV1-$gag_{372}$, -$gag_{366}$, -$gag_{344}$, -$gag_{322}$ did not. Polypeptide domains of HIV-2 gag protein, p16 MA (matrix protein), p26 CA (capsid protein) and p12 NC (nucleic acid binding protein) are shown on the top of diagram. C on HIV-$gag_{425}$ denotes cysteine which represents the zinc finger domain.

The C-terminus of the gag protein, including the zinc finger domain, is not necessary for particle formation (FIG. 1). Therefore, it is possible to replace the C-terminus of the gag precursor protein with other sequences without losing the ability of the gag protein to form virus-like particles. The gag protein has the unique ability to form particles in the absence of all other components of the virus, and the chimeric gag particles are devoid of genomic RNA. Formation of chimeric gag particles containing the major neutralizing epitope (V3) and/or the CD4-binding domain (CD4BD) of gp120 may allow effective generation of HIV-neutralizing antibodies; antigens presented in a particulate form may enhance immunogenicity of the epitopes and multiple copies of specific epitopes can be presented. Furthermore, secreted chimeric particles can be safely and easily collected and purified from cell culture media by centrifugation.

In this application, we show mapping of essential domains of gag protein for particle formation and construction of six different chimeric gag genes containing either the V3 loop (V3) or the V3 loop plus the CD4 binding domain (V3+CD4BD) of gp120 from HIV-1 or HIV-2. These constructs were expressed in insect cells using a baculovirus expression vector. The minimum length of HIV-2 gag to form particles is 376 amino acids and 373rd position proline is essential for the particle formation. The chimeric gene construction reveals that only certain combinations of fusion proteins are expressed, assembled as virus-like particles, and retain antigenicity and immunogenicity of both gag and env epitopes.

The present invention provides a map of the minimum length of HIV-2 gag gene sequences which are required for the gag particle formations using deletion mutagenesis.

An HIV-2 gag gene sequence which is deleted up to 143 amino acids at the C-terminus from the 519 amino acid sequence, and which retains 376 amino acids at the N-terminus is the minimum protein for the gag particle formation of HIV-2. In contrast, deletion of four more amino acids to 372 amino acids at the N-terminus, eliminated gag particle formation.

Site-directed mutagenesis revealed that the proline at amino acid position 373rd, but not 375th and 377th, is essential for the particle formation.

Figure 2:
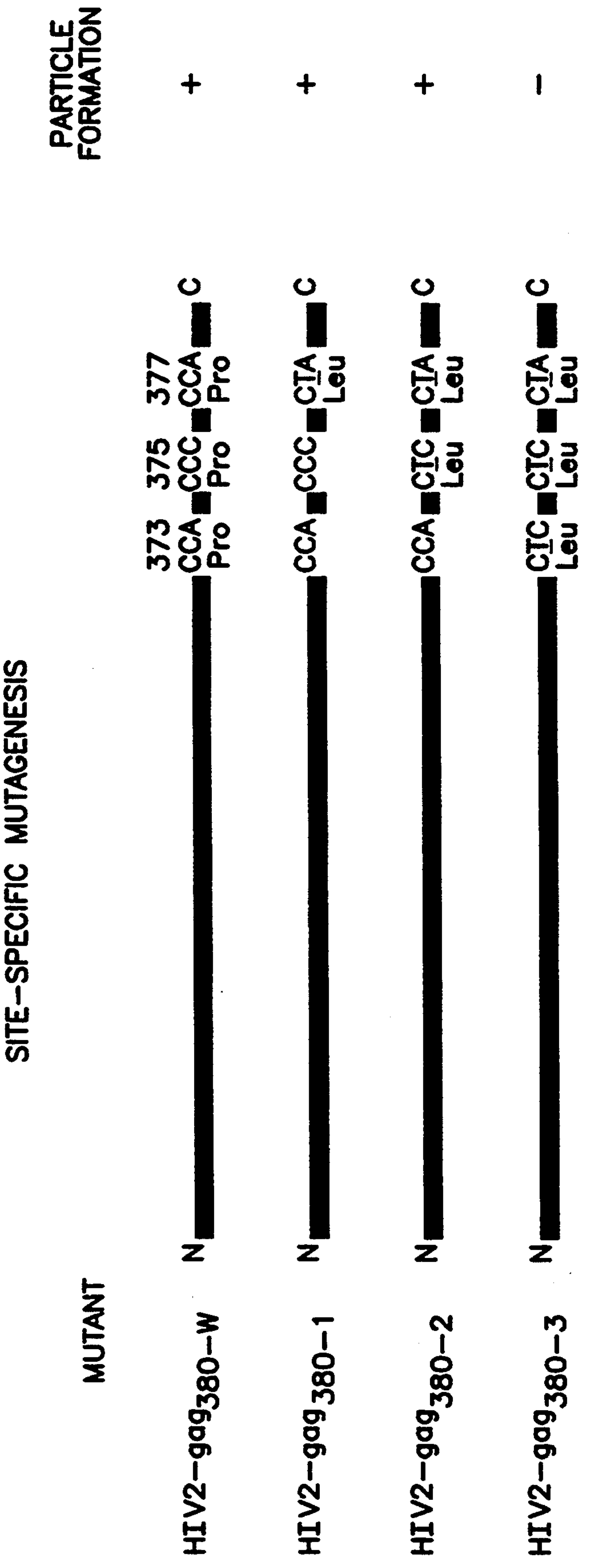
FIG. 2 shows site-specific mutants of HIV-2-$gag_{380-W}$ gene with particle formation. Three prolines located at amino acid position 373, 375 and 377 at the C-terminus of gag mutant, HIV-2-$gag_{380-W}$, were substituted with 1, 2 or 3 leucine residues by site-directed mutagenesis using PCR and expressed in SF9 cells. The subsitution of up to two prolines did not affect the gag particle formation, whereas changing of all three prolines resulted in the failing of particle formation as examined by electron microscopy.

To map the gag protein domain(s) which is essential for the particle formation, both deletion and site-directed mutagenesis were carried out. FIG. 1 clearly demonstrates that 376 amino acids at the N-terminus are required for the particle formation. In contrast to previous reports, the zinc-finger domain at the C-terminus is not required for gag particle formation. Furthermore, the present site-specific mutants showed that the 373rd position proline is essential for the particle formation as shown in FIG. 2. The results in FIG. 1 and FIG. 2 indicate that one must retain uninterrupted 1,128 base pairs of HIV-2 gag reading frame is essential to package foreign epitopes into gag particles.

The present inventors have constructed six different combinations of chimeric genes by coupling the truncated HIV-2 gag gene which will code for 425 amino acids to the neutralizing domain (V3) on to the neutralizing domain (V3) and the CD4 binding domains (V3+CD4BD) of gp 120 env gene sequences from HIV-1 or HIV-2. Such a preparation has led to the present invention.

The env gene sequences were either inserted into the middle of the gag gene or at the 3′ terminus of the gag gene. Virus-like particles were formed by chimeric gene products only when the env gene sequences were linked to the 3′ terminus of the gag gene. Insertion of env gene sequence in the middle of the gag gene resulted in high level chimeric gene expression but without the formation of virus-like particles.

In particular, three different chimeric proteins: (1) gag (425 amino acids) with HIV-1 V3 (91 amino acids), (2) gag with HIV-2 V3 (90 amino acids) and (3) gag with HIV-2 V3+CD4BD (198 amino acids) formed virus-like particles that were secreted into the cell culture medium (cf. Table 1).

TABLE 1

Comparison of particle formation and yield of chimeric fusion proteins

| Recombinant Viruses | Particle formation* | Sucrose concentration** | Yield/5 × $10^8$ cell/liter |
|---|---|---|---|
| AcNPV-HIV-2gag | + | 40% | 30 mg |
| Ac-gagM-1V3 | — | — | — |
| Ac-gagC-1V3 | + | 50% | 6 mg |
| Ac-gagM-2V3 | — | — | — |
| Ac-gagC-2V-3 | + | 50% | 25 mg |
| Ac-gagC-2V3 + 2CD4BD | + | 60% | 2 mg |

*Plus sign (+) denotes virus-like particles were recovered from the cell culture media.
**Virus-like particles were banded on top of the sucrose solutions after ultracentrifugation.

The present invention also provides a recombinant baculovirus containing chimeric gene.

Recombinant baculovirus of the present invention can be prepared by using Autographa Californica nuclear polyhedrosis virus (AcNPV) or *Bombyx iridexcent* virus.

The recombinant virus is obtained by inserting the chimeric gene into AcNPV genome and purified by the consecutive plaque assays to select polyhedrin negative recombinant virus. The AcNPV inserted with gag of HIV-2 is deposited with the ATCC as a deposit number VR2314, AcNPV inserted with gag of HIV-2 and V3 of HIV-1 as a number VR2316, AcNPV inserted with gag of HIV-2 and V3 of HIV-2 as a number VR2317, on Feb. 26, 1991. These are guaranteed for furnishing for the purpose of research.

The insect cells selected from the group consisted of *Spodoptera frugiperda* cells, *Mamestra brassica* cells, *Trichoplusia ni* cells, *Bombyx mori* cells and *Bombyx mori* silkworm cells were infected with recombinant baculovirus obtained as above to express gag chimeric protein.

The chimeric gag particles of the invention elicit neutralizing antibodies in the rabbits which completely block HIV infection.

The chimeric gag particles of the invention can be used for the antigen of a potential anti-AIDS vaccine or as a diagnostic reagent. A vaccine prepared with the chimeric gag particles according to the present invention would be useful to induce a specific immune reaction against an immunogen when the vaccine is used at pre- or post-exposure of HIV to assist in preventing an HIV infection, or may be used for immunotherapeutic treatment.

The vaccine of the invention may include a conventional absorbent, stabilizer, adjuvant, carrier and the like, and may be administered through a conventional route.

Other features of the invention will become apparent in the course of the following description of the exemplary embodiments which are given for illustration of the invention and are not intended to be limiting thereof.

EXAMPLES

Example 1

<Preparation of plasmids>

Autographa californica nuclear polyhedrosis virus (AcNPV) and recombinant AcNPV were grown and assayed in *Spodoptera frugiperda* (SF9) cell monolayers using complete TNM-FH medium containing 10% fetal bovine serum at 27° C. as described in Adv. Virus Res. 35, 177–192, 1988. Wild type AcNPV DNA was purified by the method of Smith and Summers (Virology 89, 517–527, 1978).

Plasmids pHXB-2D and p1BM containing the entire HIV-$I_{HXB2D}$ and HIV-$2_{NIHZ}$ genomes respectively were obtained from Dr. R. Gallo (National Institutes of Health, Bethesda, Md.). The recombinant plasmids pUC19-gp120-NSS, pUC18-gp120 and pUC19-GAG containing full-length cDNA copies of the HIV-1 env, HIV-2 env and a truncated gag gene of HIV-2 (which codes 425 amino acids) respectively were subcloned from pHXB-2D and p1BM as described by the inventors in Virology 179, 874–880, 1990.

Example 2

<Preparation of chimeric gene>

To subclone the V3 and V3+CD4B of the HIV-1 and HIV-2 env genes into pUC19-GAG recombinant plasmid pUC19-gp120-NSS and pUC19-gp120 were used as templates and the specific regions were amplified with appropriate oligonucleotide primers. That is to say, plasmids pUC19-gp120-NSS (HIV-1) and pUClS-gp120 (HIV-2) were used as templates for polymerase chain reaction (PCR) amplification of an HIV-1 DNA fragment corresponding to the V3 domain (91 amino acids, position 273–363) and HIV-2 DNA fragments corresponding to a V3 equivalent domain (90 amino acids, position 294–383) and V3+CD4BD (19 amino acids, position 294–491). All primers were designed to create a BglII restriction site at the 5′ end so that gp120 DNA fragments could be inserted into the BglII site of pUC19-GAG.

The HIV-1 V3 DNA fragment was amplified using L-1:(5′-CGAAGATCTGTCAATTTCACGG-3′) [SEQ. ID NO:1] and L-2(5′-GCAGATCTTTGCTTAAAGATTA-3′) [SEQ. ID NO:2] primers, which are complementary to nucleotides 816 through 836 and 1075 through 1089, respectively. The V3+CD4BD DNA fragment of HIV-1 was generated from pUC19-gp120-NSS BglII digestion at nucleotide positions 816 and 1398 of gp120. Primers L-3:(5′-CGAGATCT CATTGTTAAGAGGCC-3′) [SEQ. ID NO:3] and L-4(5′-GCAGATCTTCTGCAGTTAGTCC-3′) [SEQ. ID NO:4], complementary to nucleotides position 879 through 893 and 1135 through 1149 of HIV-2 gp 120, respectively, were used to synthesize the HIV-2 V3 DNA fragment. Primers L-3 and L-5:(5′-GCAGATCTCTTTACTGATGTAG-3′) [SEQ. ID NO:5], which is complementary to nucleotides 1459 through 1473 of HIV-2 gp120 were used to synthesize the HIV-2 V3+CD4BD DNA fragment. PCR was performed according to the procedures provided with the Geneamp kit (Norwalk, Conn.). Briefly, 20 ng of linearized gp120 DNA was added to 100 μl PCR reaction mixture (10 mM Tris-HCl, 50 mM KCl, 1.5 mM $MgCl_2$ and 0.01% gelatin) containing 20 μM each dNTP, 2.5 Units of Taq polymerase, and 20 μM of each oligonucleotide primer.

Figure 3:
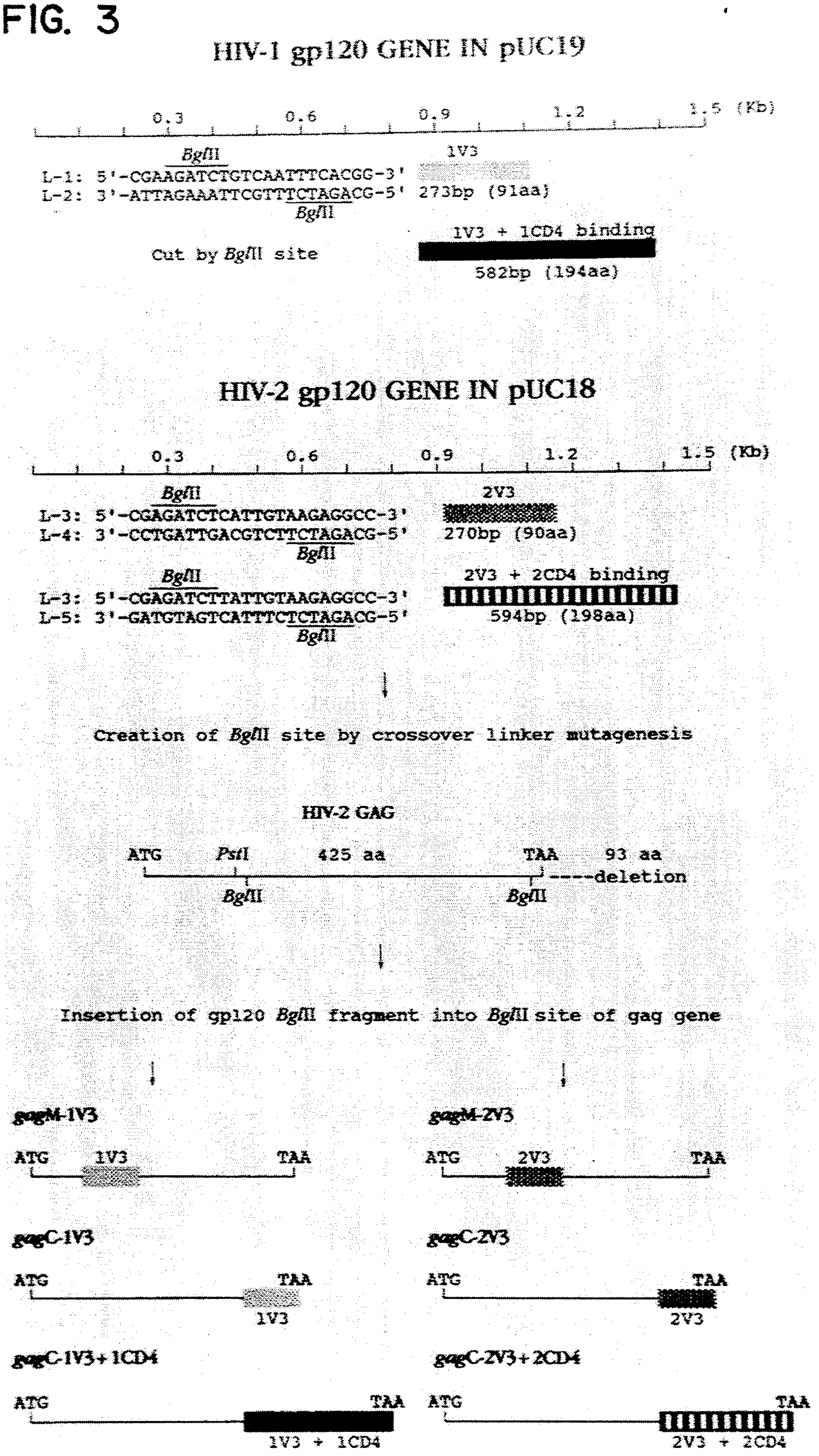
FIG. 3 shows construction of chimeric gag-env genes. BglII fragments containing the V3 (amino acid positions 273–363) or V3+CD4BD (amino acid position 294–491) from HIV-2 gp120 were amplified by PCR. The V3+CD4BD sequences of HIV-1 were directly isolated from pUC-gp120-NSS by BglII digestion. To insert these BglII fragments at the 3'-terminus of the HIV-2 gag gene without the protease sequences, two BglII sites were created by crossover linker mutagenesis, one downstream of the PstI site and another at the C-terminus just upstream of the stop codon. BglII fragments carrying either V3 or V3+CD4BD from HIV-1 or HIV-2 were inserted into the middle of the 3'terminal BglII site. A total of six constructs were made. The dot-hatched box and solid black box represent the V3 and CD4BD of HIV-1 gp120, respectively. The checkered box and the box with vertical lines represent the V3 and V3+CD4BD of HIV-2 gp120, respectively. The number of amino acids presented in each fragment is indicated.

The V3 and V3+CD4BD genes were amplified for 30 PCR cycles (94° C. for 1 min., 45° C. for 3 min.). The chimeric gag gene constructs containing the V3 and V3+CD4BD fragments were confirmed by dideoxy DNA sequencing of double stranded DNA, using the Sequence Kit (trademark of United States Biochemical Corporation).

gagM-1V3, gagC-1V3, gagC-1V3+1CD4BD, gagM-2V3, gagC-2V3, gagC-2V3+2CD4BD chimeric genes were prepared by the above method. The numbers 1 and 2 in front of V3 and CD4BD denote genes from HIV-1 and HIV-2 respectively, gagM denotes the chimeric gene inserted into the middle of the gag gene, and gagC denotes the chimeric gene inserted into the terminus of the gag gene. The procedure for generation of the present chimeric gene is shown briefly in FIG. 3.

Example 3

<Production of Recombinant Baculovirus>

The chimeric genes obtained from the Example 2 were isolated after digestion with BamHI and inserted into the baculovirus transfer vector pAcYM1. SF9 cells were co-transfected with mixtures of infectious wild type AcNPV DNA (1 μg) and recombinant plasmid DNAs (4 μg) using standard procedures (Adv. Virus Res., 35, 177–192, 1988).

Among the recombinant baculoviruses obtained from the above procedure, AcNPV carrying gag of HIV-2 (hereinafter called 'AcHIV2GAGYK') was deposited as deposit number VR2314, AcNPV carrying gag of HIV-2 and V3 of HIV-1 (hereinafter called 'AcHIV2-GAG+1V3YK') as deposit number VR2316, and AcNPV carrying gag of HIV-2 and V3 of HIV-2 (hereinafter called 'AcHIV2GAG+2V3YK') as deposit number VR2317 with the American Type Culture Collection (ATCC) on Feb. 26, 1991. The deposits are guaranteed for furnishing of samples for the purpose of research.

After incubation of recombinant baculovirus at 27° C. for 4 days, culture supernatants were harvested and titrated on 80% confluent monolayers of SF9 cells. To obtain polyhedrin-negative recombinant AcNPV, the plaques lacking polyhedra were picked, purified by three consecutive plaque assays, and used to produce virus stock of $2\times10^8$ PFU/ml.

Example 4

<Expression of Chimeric particles>

SF9 cells were infected with either wild type AcNPV or recombinant AcNPV carrying chimeric genes at multiplicities of infection of 5 PFU/cell and incubated at 27° C. After appropriate incubation times (usually 3 to 4 days), cells were harvested and washed twice with PBS. Whole cell lysates were prepared by resuspending the cell pellet in water and adding an equal volume of 2× dissociation buffer (10% beta-mercaptoethanol, 10% SDS, 25% glycerol, 100 mM Tris-HCl, pH 7.0, 0.04% bromophenol blue). Cell lysates were analyzed by electrophoresis in 12% polyacrylamide gel containing SDS (SDS-PAGE) and the protein bands were visualized by staining with Coomassie blue (Nature 227, 283–303, 1987).

Western blot analyses were then performed using sera from AIDS patients and the Bio-Rad Immune Blot AK system. The results are shown in FIG. 4.

Figure 4B:
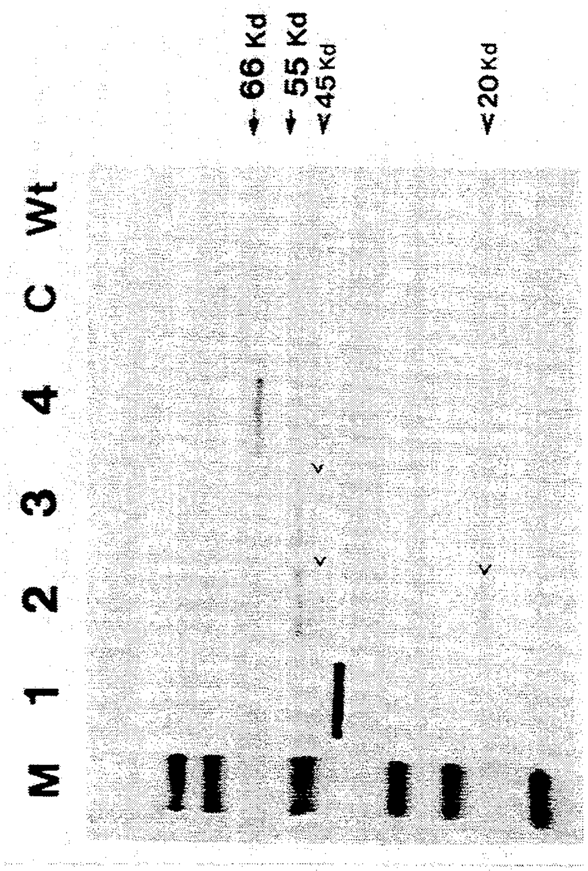
FIGS. 4A–4B shows expression of chimeric gag-env proteins in SF9 cells infected by recombinant baculoviruses. Recombinant baculovirus infected SF9 cell lysates were analyzed by SDS-PAGE and proteins were stained with Coomassie blue (A) or detected by Western blots with pooled sera from AIDS patients, Lanes 1–4: recombinant viruses AcNPV-HIV-2gag, Ac-gagM-1V3, Ac-gagC-1V3, and Ac-gagC-1V3+1CD4. The chimeric gag-env particles released into the culture supernatant were purified by centrifugation in 20–60% discontinuous sucrose density gradients, subjected to SDS-PAGE and detected by Coomassie blue staining (C) and Western blot (D). Lane 1: Purified gag particle; Lanes 2–4 : Purified gagC-1V3, gagC-2V3 and gagC-2V3+2CD4 chimeric particles; M, Marker proteins; C, uninfected cell control; Wt, wild-type AcNPV-infected cells. The major fusion protein P55 and P66 are indicated with arrows and possible cleavage products are indicated by open arrows.
Figure 4A:
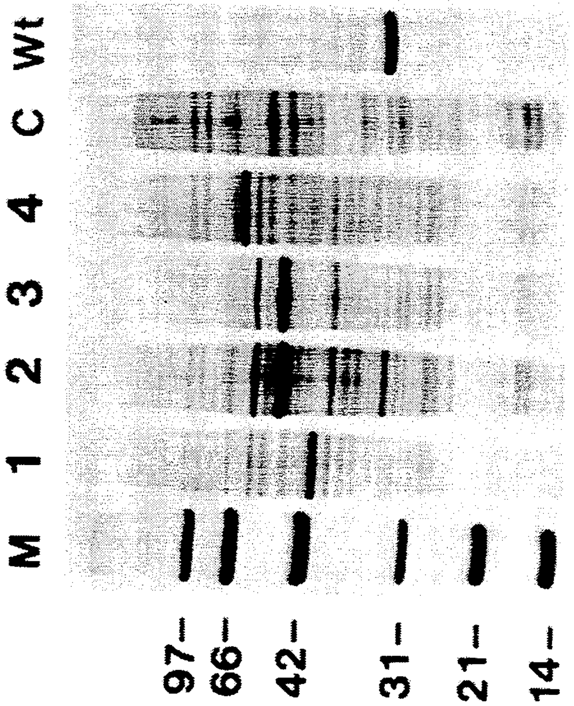
Figure 4D:
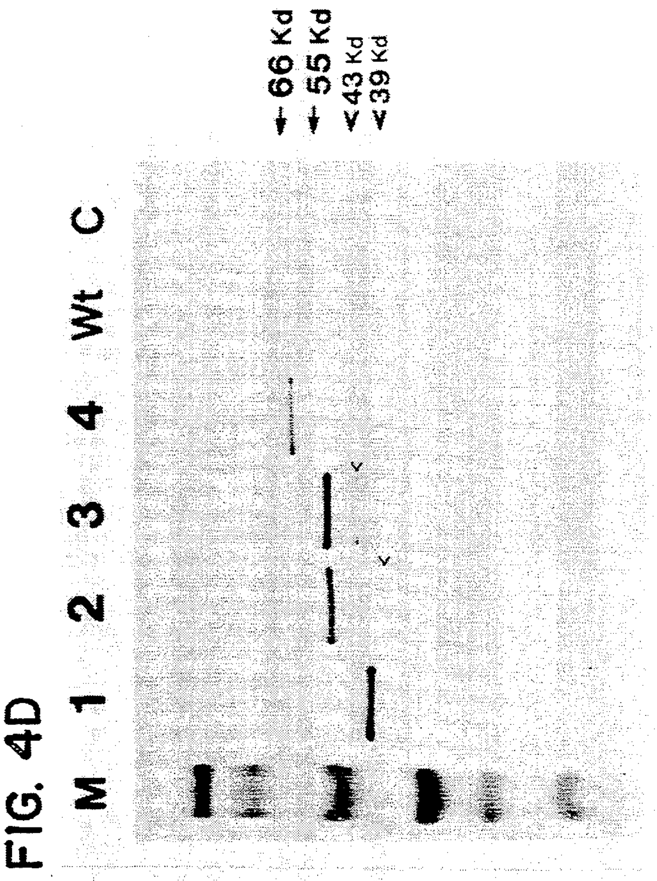
Figure 4C:
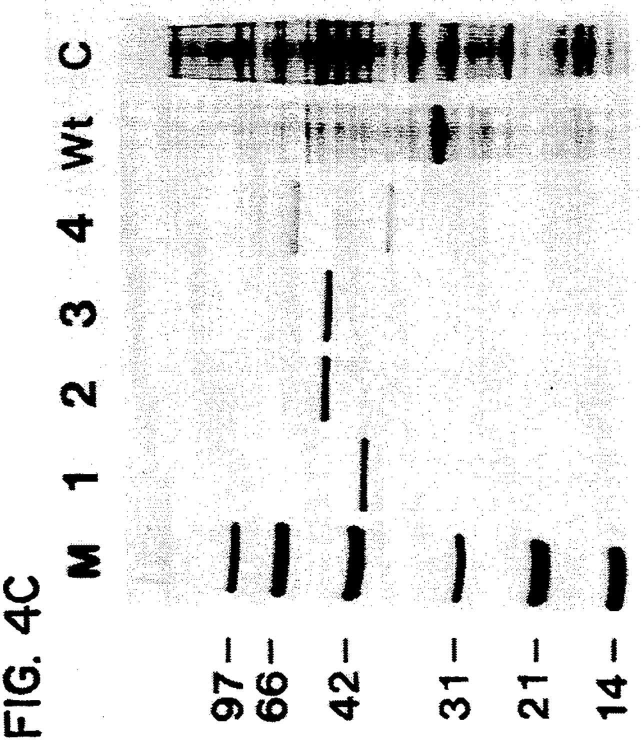

FIG. 4A shows the proteins produced by recombinant baculoviruses Ac-gagM-1V3, Ac-gagC-1V3 and Ac-gagC-1V3+1CD4BD. Since the original HIV-2 gag protein has 93 amino acids deleted from the C-terminus, an insertion of V3 (91 amino acids) or V3+CD4BD (194 amino acids) of HIV-1 gp120 into the gag gene would be expected to produce proteins of 55 KDa and 66 KDa, respectively.

As shown in FIG. 4A, strongly stained protein bands migrating at either 55 KDa or 66 KDa were observed in the lysates of SF9 cells infected with Ac-gagM-1V3 (lane 2), Ac-gagC-1V3 (lane 3) and AC-gagC-1V3+1CD4BD (lane 4) but were not present in lysates of mock or wild type baculovirus-infected cells.

Western blot analysis revealed that both the p55 and p66 fusion proteins were recognized by pooled HIV-1 positive human sera (FIG. 4B, lanes 2, 3, and 4). No specific reaction was observed with mock- and wild type AcNPV-infected cells.

The results clearly demonstrate that insertion of either HIV-1 V3 or V3+CD4BD into the gag protein resulted in expression of proteins at levels at least as high as that of recombinant AcNPV-HIV-2gag alone (FIG. 4A, lane 1).

Similar results were obtained when three other recombinant baculoviruses containing the V3 and V3+CD4BD genes from HIV-2 gp120, Ac-gagM-2V3, Ac-gagC-2V3, and Ac-gagC-2V3+2CD4BD were analyzed.

Example 5

<Purification of Chimeric particles>

The cell culture fluids obtained from the Example 4 were collected after centrifugation at 1,000×g for 20 min. Chimeric particles in the culture supernatant were collected by ultracentrifugation in a Beckman SW 28 rotor at 80,000×g for 1 hr and resuspended in PBS containing 0.1% Tween 20, 10 μg/ml aprotinin and stored at 4° C. A band containing gag particles was collected from a 20–60% discontinuous sucrose gradient, diluted at least 10-fold with PBS and pelleted in an SW28 rotor at 80,000×g for 1 hour. The pellet was gently suspended in PBS. gagC-1V3 and gagC-2V3 particles were recovered from the 50% sucrose cushion, whereas gagC-2V3+2CD4BD chimeric particles banded on top of the 60% sucrose cushion. The results of the morphology of sucrose gradient purified particles by transmission electron microscopy using uranyl acetate staining are shown in FIG. 5.

HIV-2 gag particle were spherical (FIG. 5A), had diameters of approximately 100 nm, and were similar to those of mature HIV-1 particles budding from HIV-1 infected cells. The chimeric particles gagC-1V3 (FIG. 5B), gagC-2V3 (FIG. 5C) and gagC-2V3+2CD4BD (FIG. 5D) exhibited morphologies similar to the gag particles. The peripheral granular material frequently showed striations with a periodicity suggesting a helical arrangement. It formed a shell-like layer probably inside a lipid membrane and was presumably rigid. The only difference between the gag particles and chimeric gag particles was that the chimeric gag particles were slightly larger with approximate diameters of 130 nm, similar to the diameter of mature HIV-1 particles.

Experimental Example 1

<Antigenity of Chimeric gag Particles>

Antigenicity of chimeric gag particles was investigated by immunoblot analysis. Purified chimeric gag particles were subjected to SDS-PAGE and analyzed by Western blotting with rabbit antisera directed against HIV-1 and HIV-2 gp120 and $^{125}I$-labeled protein A. The results are shown in FIG. 6. In this FIG. 6, lane 1 is HIV-2 gag protein; lane 2, gp120 protein; lane 3, chimeric gagC-1V3 protein; lane 4, chimeric gagC-1V3+1CD4 protein; C, cell control; and W is wild type AcNPV-infected cell control.

Figures 6A, 6B:
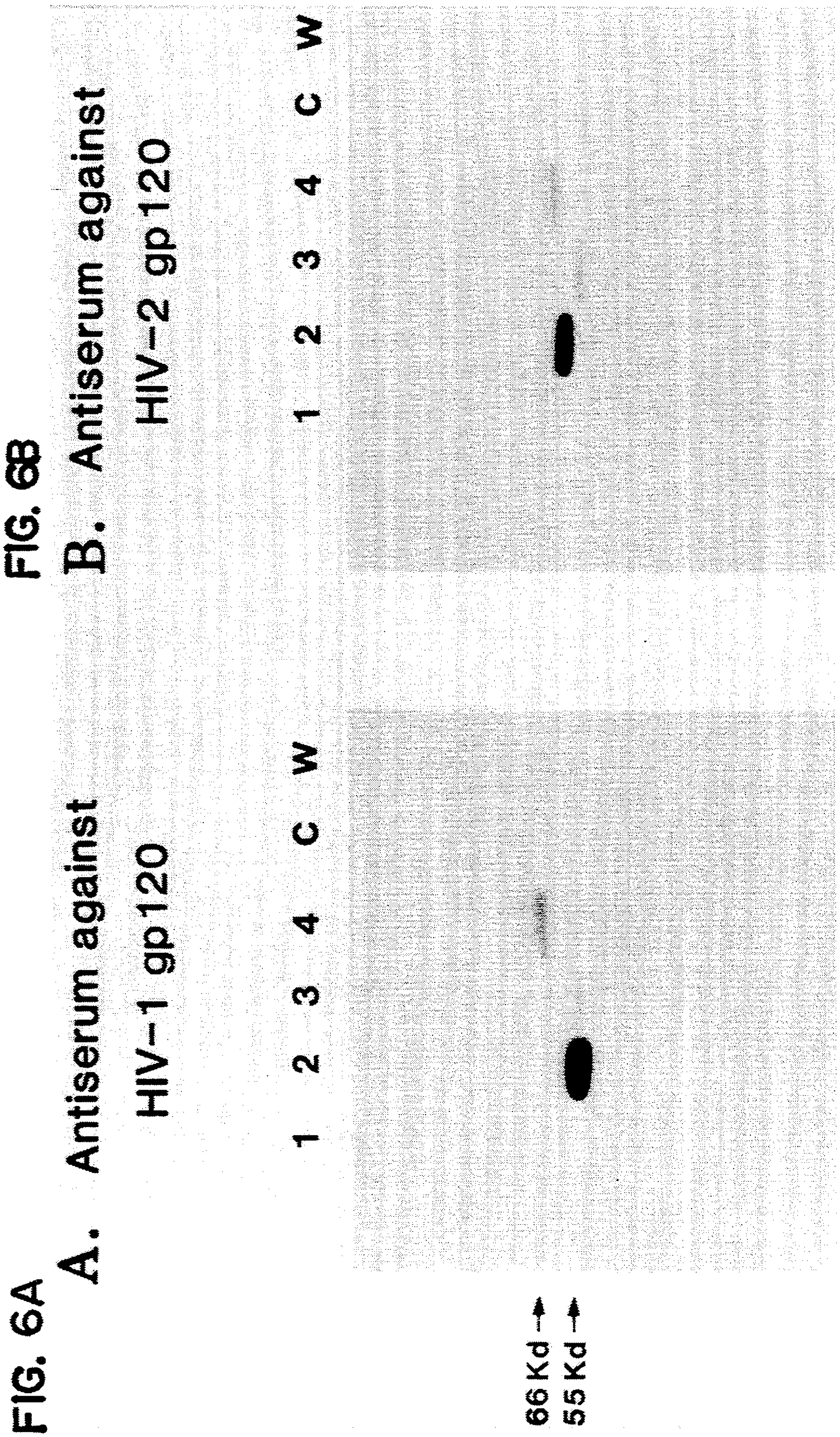
FIGS. 6A–6B shows immunoblot analysis of chimeric gag-env proteins. The chimeric gag-env proteins and gp120 of HIV-1 and HIV-2 were subjected to SDS-PAGE and electro-transferred to nitrocellulose filters. Filters were incubated with rabbit antisera specific for HIV-1 gp120 (a) and HIV-2 (b) and with $^{125}$I-labeled protein A. Lane 1: HIV-2 gag protein; lane 2, gp120 protein; lane 3, chimeric gagC-1V3 protein; lane 2, gp120 protein; lane 3, chimeric gagC-1V3 protein; lane 4, chimeric gagC-1V3+1CD4 protein; C, cell control; W, wild type AcNPV-infected cell control. The rabbit antisera against HIV-1 and HIV-2 gp120 have been described elsewhere.

The HIV-2 gag protein was not recognized by anti-gp120 sera (FIG. 6A and B, lane 1) while the non-glycosylated forms of gp120 of HIV-1 and HIV-2 showed strong reactivity with their corresponding antisera (FIG. 6A and B, lane 2). The 55 KDa and 66 KDa fusion proteins were specifically recognized by rabbit antisera against HIV-1 or HIV-2 gp120s (FIG. 6A and B, lanes 3 and 4). The results clearly demonstrate that the chimeric proteins can be detected by antiserum specific for gp120 and reaffirm that inserted sequences of V3 or V3+CD4BD are antigenic.

Experimental Example 2

<Immunogenicity of Chimeric gag-V3 Particles>

In order to examine the capacity of particles to induce antibodies to both gag and env proteins of HIV, rabbits were immunized four times at 4 week intervals with purified gagC-IV3 and gagC-2V3 chimeric particles. The immune rabbit sera were collected 2 weeks after the last immunization and tested for their ability to recognize gp120 of HIV-1 and HIV-2.

Figure 7B:
FIGS. 7A–7B Western blot analysis using rabbit antisera made against chimeric gag-env particles. (A) Anti-gagC-1V3 serum recognized non-glycosylated gp120 protein of HIV-1. Lane 1, HIV-2 gag protein; Lane 2, non-glycosylated gp120 protein of HIV-1. (B) Anti-gagC-2V3 serum recognized non-glycosylated gp120 protein of HIV-2. Lane 1, HIV-2 gag protein; lane 2, non-glycosylated gp120 protein of HIV-2. Wt, wild-type AcNPV-infected cells at day 3 postinfection (p.i.). C, cell control. Sera were diluted 1:200 and the Bio-Rad immuno-Blot AK detection system was employed.
Figure 7A:
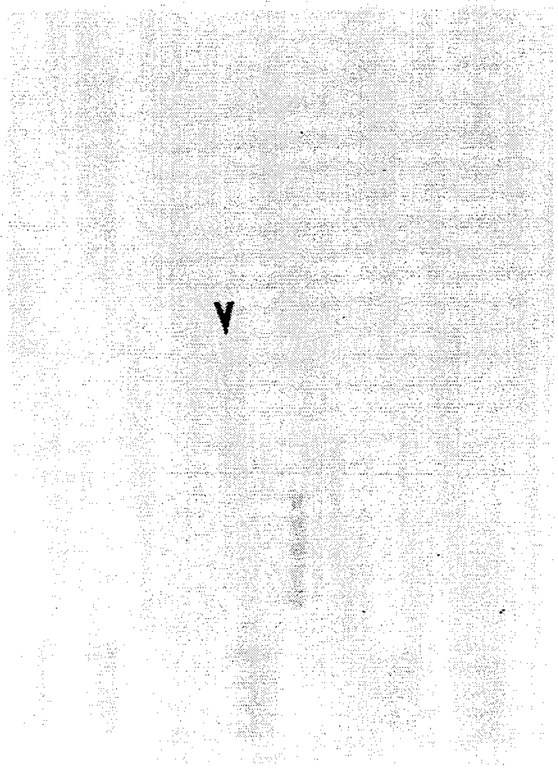

As shown in FIG. 7, the antisera made against both gagC-1V3 and gagC-2V3 chimeric particles recognize not only carrier HIV-2 gag protein (FIG. 7A, B, lanes 1) but also non-glycosylated gp 120 of HIV-1 (FIG. 7A, lane 2) and HIV-2 (FIG. 7B, lane 2).

In contrast, neither wild type AcNPV infected SF9 cells nor uninfected SF9 cells contain proteins which were recognized by the antisera. These results clearly demonstrate that the V3 loop domain in chimeric gagC-1V3 and gagC-2V3 particles retain both antigenic and immunogenic properties.

Experimental Example 3

<Immune Sera Against Chimeric gag-V3 Particles of HIV-1 or HIV-2 Neutralize Virus Infectivity in Vitro>

Rabbit anti-sera directed against chimeric particles were used to neutralize the infectivity of HIV as assayed by reverse transcriptase (RT) activity and gag p24 production. Rabbits were immunized four times at one month intervals with intramuscular injections of 25 μg of the density gradient-purified chimeric gag particles. Rabbit anti-gagC-1V3 and anti-gagC-2V3 sera (25 μl) were mixed with 100 μl of virus which represented 5000 $TCID_{50}$ of HIV-$1_{IIIB}$ or 8000 $TCID_{50}$ of HIV-$2_{ROD}$, respectively, and the mixtures were used to infect H9 cells. The amount of p24 gag protein and reverse transcriptase (RT) activity in the culture media were assayed as quantitation of virus production on different days after infection (days 1–16) and the levels were compared with those of control samples in which virus was incubated with preimmune sera or rabbit anti-gp120 serum.

FIG. 8 shows that both rabbit anti-gagC-1V3 and anti-gagC-2V3 sera contained antibodies capable of neutralizing HIV infection of H9 cells. By day 9 postinfection, antisera to gagC-1V3 and gagC-2V3 chimeric particles completely blocked the production of HIV-1 and HIV-2, respectively. However, at day 12 post-infection, a small amount of HIV-1 was detected in cultures treated with anti-gagC-1V3 serum (FIG. 8, a and b). In contrast, the antisera to gag-2V3 chimeric particles completely neutralized HIV-2 infectivity (FIG. 8, c and d). No reduction in RT and p24 gag protein production were observed with pre-immune sera. Rabbit anti-gp120 sera of HIV-2 showed stronger neutralizing activity of HIV-$1_{ROD}$ than rabbit anti-gp120 sera of HIV-1 against HIV-$1_{IIIB}$ (FIG. 8).

From the above, it is recognized that the chimeric protein according to the present invention showed excellent neutralizing activity against HIV-1 and HIV-2.

What is claimed is:

1. A recombinant Gag-Env chimeric polypeptide particle of human immunodeficiency virus, comprising:

an HIV-2 Gag polypeptide selected from the group consisting of HIV-2 Gag polypeptides which extend from the N-terminal amino acid of Gag to a minimum of amino acid 376 and a maximum of amino acid 425 and wherein said Gag polypeptides have a proline at amino acid 373, 375 or 377; and an Env polypeptide from HIV comprising the V3 loop domain of gp120; the Env polypeptide linked to the C-terminus of the Gag polypeptide.

2. The Gag-Env chimeric polypeptide particle according to claim 1, wherein the Env polypeptide comprises the V3 loop domain of gp120 and the CD4 binding site.

3. The Gag-Env chimeric polypeptide particle according to claim 1, wherein the Gag-Env chimeric polypeptide is expressed in an insect cell by a recombinant baculovirus comprising a chimeric gag-env gene encoding the Gag-Env chimeric polypeptide.

4. The Gag-Env chimeric polypeptide particle according to claim 3, wherein the recombinant baculovirus is ATCC deposit number VR2316 or VR2317.

* * * * *

UNITED STATES PATENT AND TRADEMARK OFFICE
CERTIFICATE OF CORRECTION

PATENT NO. : 5,443,828

DATED : 08/22/95

INVENTOR(S) : Kang et al.

It is certified that error appears in the above-identified patent and that said Letters Patent is hereby corrected as shown below:

Title page, item [57],
At abstract, line 1, delete "protential" and insert therefor --potential--.

At Col. 1, Line 7, insert --and-- after the word "vaccine".

At Col. 2, Line 50, delete "Figs. 4A-4B" and insert therefor --Figs. 4A-4D--.

Figure 5A:
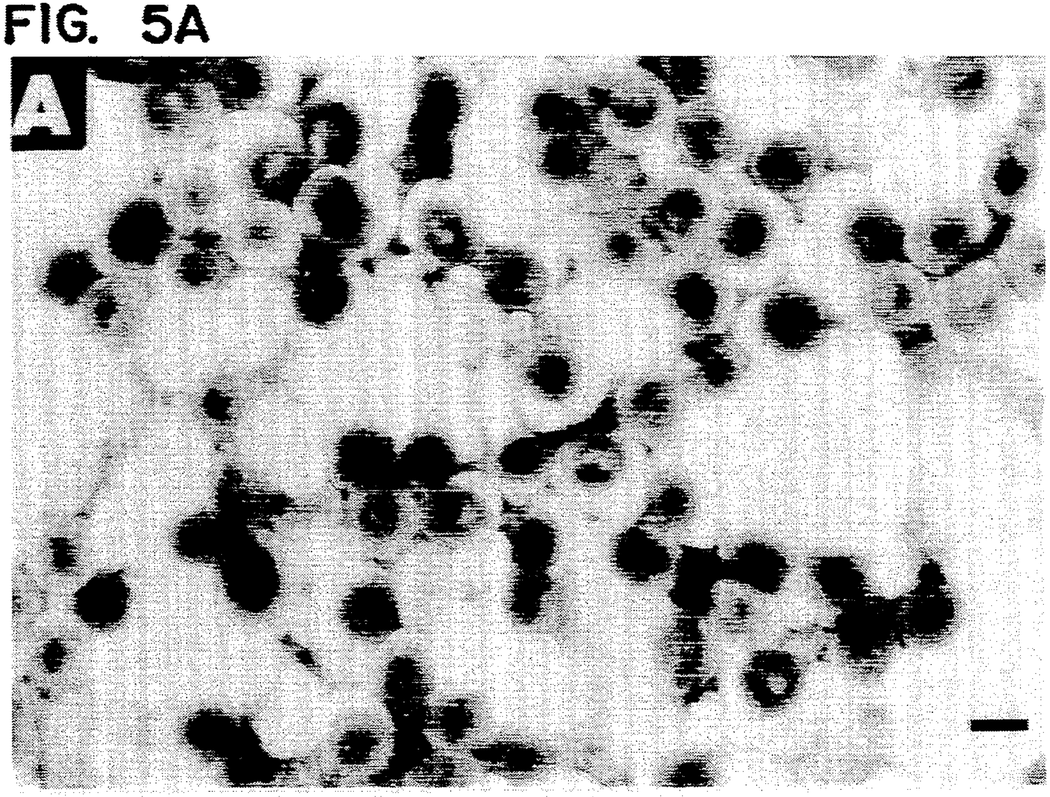
FIGS. 5A–5B shows electron micrographs of sucrose gradient-purified gag-env chimeric particles. (A) HIV-2 gag particles produced by SF9 cells infected with recombinant AcNPV-HIV-2 gag, (B) Chimeric gag-env particles produced by recombinant Ac-gagC-1V3. (C) Chimeric gag particles produced by recombinant Ac-gagC-2V3, and (D) Chimeric gag particles produced by recombinant Ac-gagC-2V3+2CD4. Samples were stained with uranyl acetate. The bar represents 100 nm.
Figure 5B:
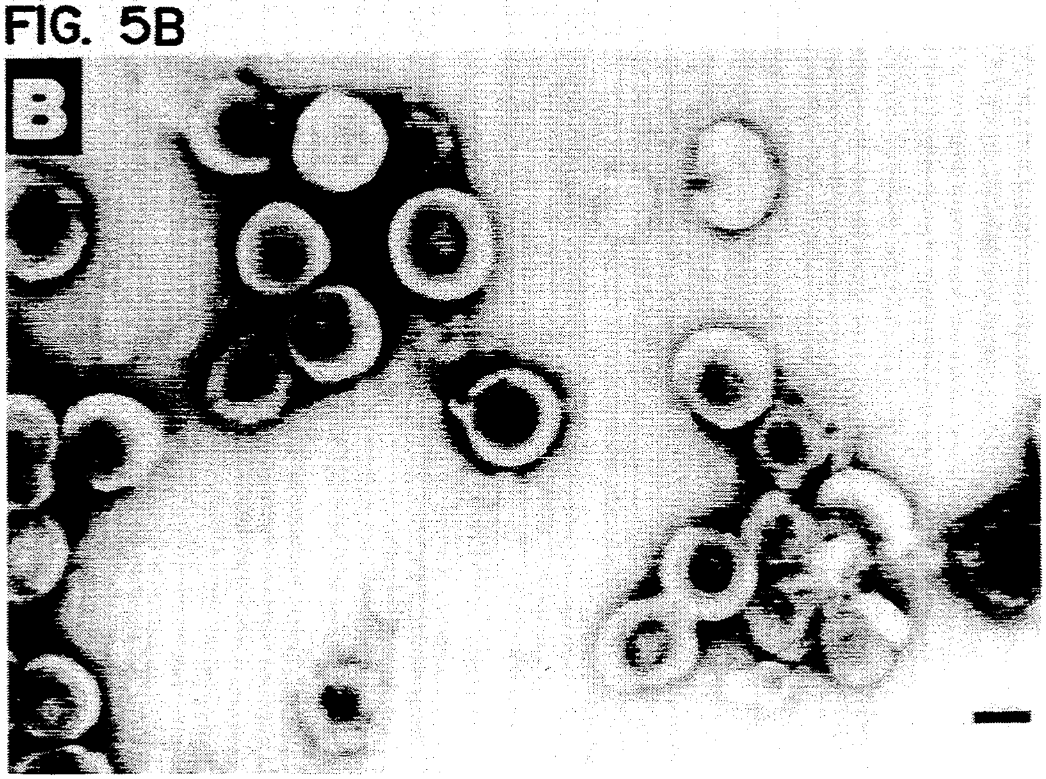
Figure 5C:
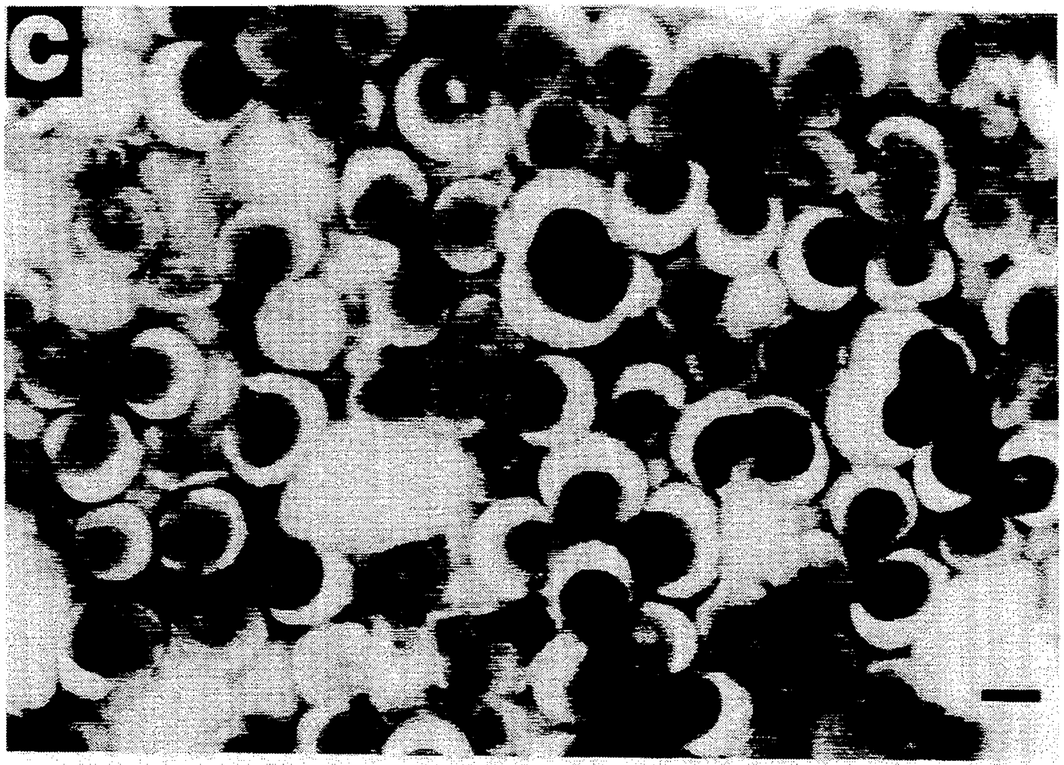
Figure 5D:
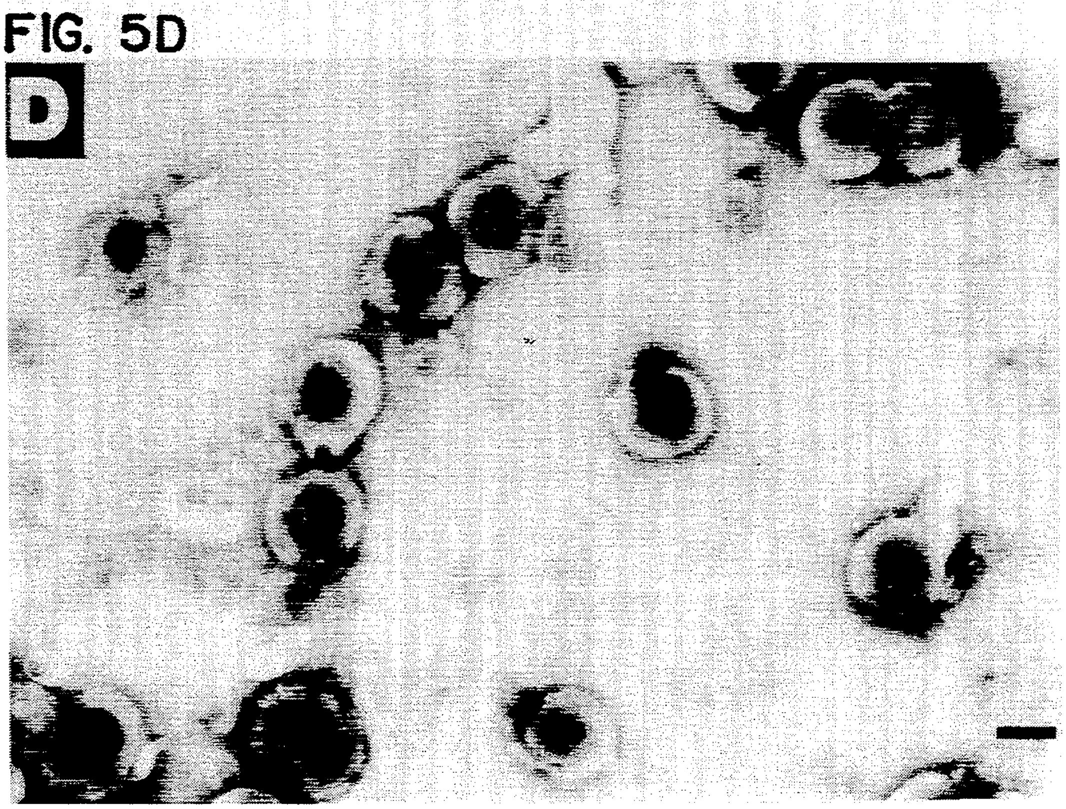

At Col. 3, Line 1, delete "Figs. 5A-5B" and insert therefor --Figs. 5A-5D--.

Figure 8A:
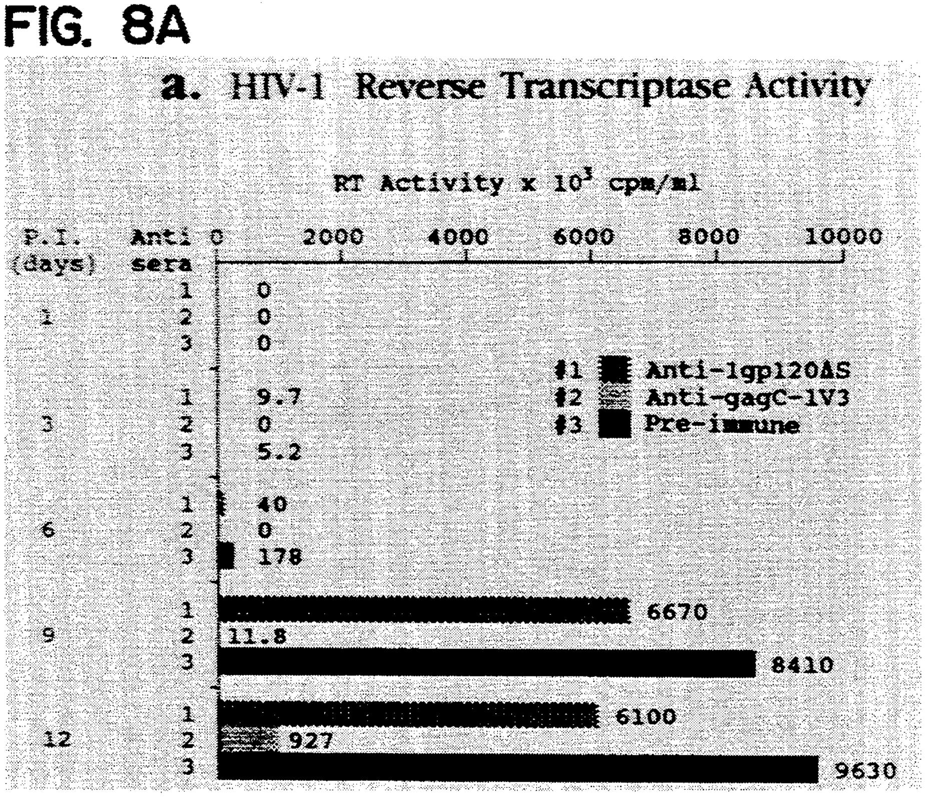
FIGS. 8A–8B shows neutralization of HIV-1$_{IIIB}$ and HIV-2$_{ROD}$ infection with immune rabbit sera. Antisera against gagC-1V3 and gagC-2V3 (HIV-2) chimeric particles were diluted and tested for neutralization of virus using reverse transcriptase and vital p24 or p 26 assays. a and b: HIV-1; and d: HIV-2. Pre-immune serum (■); V3 specific immune serum (■) from rabbits immunized with chimeric gag-V3 particles of HIV-1 or HIV-2; anti-gp120 sera(░) specific for gp120 of HIV-1 OR HIV-2. The neutralizing activity of anti-gagC-1V3 and anti-gagC-2V3 sera were determined by incubation of sera (1:5 dilution) with stock virus preparation of HIV-1$_{IIIB}$ (5000 TCID$_{50}$) or HIV-2$_{ROD}$ (8000 TCID$_{50}$) at 37° C. for 1 hour before infecting H9 cell. Viral infection was monitored by reverse transcriptase activity (a and c) and the production of HIV-1 p24(b) or HIV-2 p26(d) gag proteins at 1–16 days p.i.
Figure 8B:
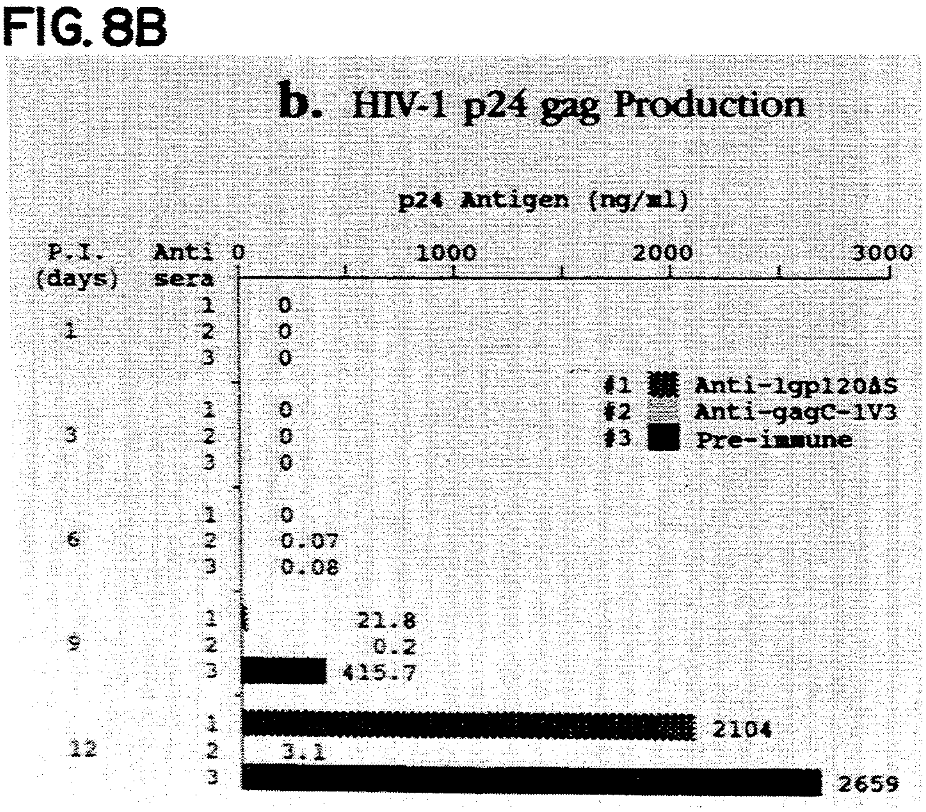
Figure 8C:
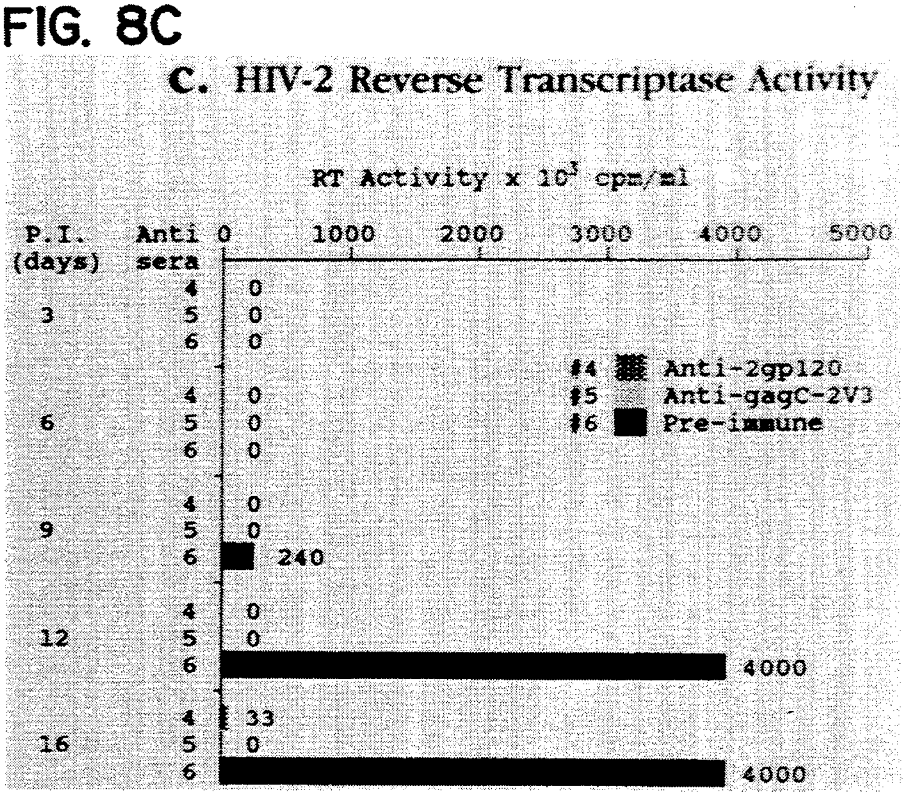
Figure 8D:
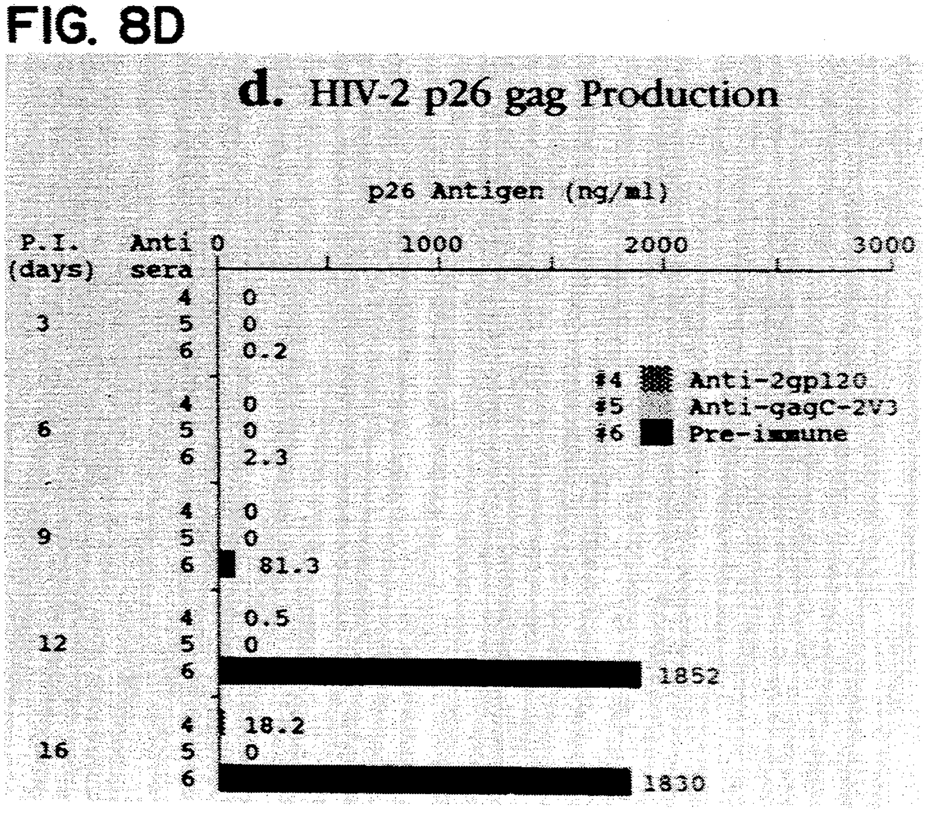

At Col. 3, Line 34, delete "Figs. 8A-8B" and insert therefor --Figs. 8A-8D--.

At Col. 4, Line 59, delete "on" and insert therefor --or--.

At Col. 6, Line 35, delete "pUC1S" and insert therefor --pUC18--.

Signed and Sealed this

Second Day of July, 1996

*Attest:*

BRUCE LEHMAN

*Attesting Officer* *Commissioner of Patents and Trademarks*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: HIV-1

( i x ) FEATURE:
( A ) NAME/KEY: L-1 oligonucleotide primer complementary to nucleotides 816 through 836 of HIV-1 V3 DNA fragment
( B ) LOCATION: 816..836

( x i ) SEQUENCE DESCRIPTION: SEQ ID NO:1:

CGAAGATCTG TCAATTTCAV GG 22

-continued ( 2 ) INFORMATION FOR SEQ ID NO:2:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: HIV-1

( i x ) FEATURE:
( A ) NAME/KEY: L-2 oligonucleotide primer complementary to nucleotides 1075 through 1089 of HIV-1 V3 DNA fragment
( B ) LOCATION: 1075..1089

( x i ) SEQUENCE DESCRIPTION: SEQ ID NO:2:

GCAGATCTTT GCTTAAAGAT TA 22

( 2 ) INFORMATION FOR SEQ ID NO:3:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: HIV-2

( i x ) FEATURE:
( A ) NAME/KEY: L-3 oligonucleotide primer complementary to nucleotides 879 through 893 of HIV-2 V3 DNA fragment
( B ) LOCATION: 879..893

( x i ) SEQUENCE DESCRIPTION: SEQ ID NO:3:

CGAGATCTCA TTGTAAGAG GCC 22

( 2 ) INFORMATION FOR SEQ ID NO:4:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: HIV-2

( i x ) FEATURE:
( A ) NAME/KEY: L-4 oligonucleotide primer complementary to nucleotides 1135 through 1149 of HIV-2 V3 DNA fragment
( B ) LOCATION: 1135..1149

( x i ) SEQUENCE DESCRIPTION: SEQ ID NO:4:

GCAGATCTTC TGCAGTTAGT CC 22

( 2 ) INFORMATION FOR SEQ ID NO:5:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

-continued ( v i ) ORIGINAL SOURCE:
( A ) ORGANISM: HIV-2

( i x ) FEATURE:
( A ) NAME/KEY: L-5 oligonucleotide primer complementary to nucleotides 1459 through 1473 of HIV-2 gp120
( B ) LOCATION: 1469..1473

( x i ) SEQUENCE DESCRIPTION: SEQ ID NO:5:

GCAGATCTCT TTACTGATGT AG 22